United States Patent [19]
Kim et al.

[11] Patent Number: 6,047,210
[45] Date of Patent: Apr. 4, 2000

[54] CARDIOVERTER AND METHOD FOR CARDIOVERTING AN ATRIAL TACHYARRHYTHMIA WHILE MAINTAINING ATRIAL PACING

[75] Inventors: Jaeho Kim, Redmond; Joseph M. Bocek, Seattle, both of Wash.

[73] Assignee: Cardiac Pacemakers, Inc., Minneapolis, Minn.

[21] Appl. No.: 09/146,948

[22] Filed: Sep. 3, 1998

[51] Int. Cl.[7] .................................................. A61N 1/05
[52] U.S. Cl. ............................................................. 607/4
[58] Field of Search ........................................ 607/4, 5, 14

[56] References Cited

U.S. PATENT DOCUMENTS 5,549,641  8/1996  Ayers et al. ................................. 607/4
5,720,295  2/1998  Greenhut et al. ........................... 607/5

Primary Examiner—Jeffrey R. Jastrzab
Attorney, Agent, or Firm—Foley & Lardner

[57] ABSTRACT

An atrial cardioverter for cardioverting atria of a heart while sustaining atrial pacing of the heart. The cardioverter includes a pacer for pacing the heart in one of a plurality of modes including an atrial pacing, atrial inhibited mode, and an atrial pacing, ventricular inhibited mode, an atrial tachyarrhythmia detector for detecting an atrial tachyarrhythmia of the heart, and a mode control for changing the mode of the pacer from the atrial pacing, atrial inhibited mode to the atrial pacing, ventricular inhibited mode responsive to the atrial tachyarrhythmia detector detecting an atrial tachyarrhythmia of the heart. A cardioverter stage applies cardioverting energy to the atria responsive to the atrial tachyarrhythmia detector detecting an atrial tachyarrhythmia and after the pacer mode change.

11 Claims, 2 Drawing Sheets

CARDIOVERTER AND METHOD FOR CARDIOVERTING AN ATRIAL TACHYARRHYTHMIA WHILE MAINTAINING ATRIAL PACING

BACKGROUND OF THE INVENTION

The present invention generally relates to a method and system for cardioverting an atrial tachyarrhythmia. The present invention is more particularly directed to such a system and method which is capable of safely cardioverting an atrial tachyarrhythmia while maintaining atrial pacing.

Atrial fibrillation is probably the most common cardiac arrhythmia. Although it is not usually a life-threatening tachyarrhythmia, it is associated with strokes thought to be caused by blood clots forming in areas of stagnant blood flow as a result of prolonged atrial fibrillation. In addition, patients afflicted with atrial fibrillation generally experienced rapid and irregular beating of the heart and may even experience dizziness as a result of reduced cardiac output.

Atrial fibrillation occurs suddenly, and many times can only be corrected by discharging electrical energy into the atria of the heart of the patient. This treatment is preferably synchronized to a detected R wave of the heart in order to avoid shocking the atria during the T wave or vulnerable period of the heart. The amount of energy which may be required to successfully cardiovert the atria can be as low as one joule and as high as six joules. In most cases, energy of about two to four joules is required to cardiovert atrial fibrillation back to normal sinus rhythm (NSR).

Implantable atrial defibrillators are known which detect the presence of atrial fibrillation and provide a single cardioverting pulse of electrical energy to the atria when atrial fibrillation is detected. One such defibrillator disclosed in U.S. Pat. No. 5,207,219 applies the therapy in synchrony with a detected R wave and after a minimum cardiac cycle interval to avoid therapy application during the ventricular vulnerable period of the heart thereby preventing the induction of a lethal ventricular arrhythmia. This therapy has been found to be very effective and safe. It, however, assumes that no other therapy is being applied to the heart at the time that the defibrillator is detecting for a suitable R wave for synchronized therapy delivery.

Some patients, and particularly those with sick sinus syndrome, require continuous atrial pacing because of a dysfunctional sinus node precluding the production of intrinsic atrial activations or P waves. For those patients, the right atrium is continuously paced at a minimum or rate responsive rate. The pacing is performed in an inhibit mode to inhibit an atrial pacing pulse should a P wave be spontaneously produced by the heart.

To accommodate or treat a patient with sick sinus syndrome who also has episodes of an atrial tachyarrhythmia, such as atrial fibrillation, an atrial cardioverter must be able to both continuously pace the atria and cardiovert the atria in the presence of such pacing. Unfortunately, during atrial fibrillation, the amplitude of atrial activity becomes drastically diminished and intrinsic atrial activity may be undersensed. This essentially reduces the atrial pacing to fixed rate, non-inhibited pacing, commonly referred to as AOO pacing. Since these patients require continuous atrial pacing, disabling pacing during cardioversion is not an option, especially if the patients atria spontaneously revert out of atrial fibrillation. They would then be left with no atrial therapy at al.

As can be appreciated from the above, under these AOO pacing conditions, chaotic heart activity is evident. Not only are the atria being paced at a fixed rate, but R waves, at a rapid and irregular rate are also being produced by the heart. In order to find a safe and effective time to apply tachyarrhythmia therapy while maintaining atrial pacing, measures not heretofore known must be used. The present invention provides such measures.

SUMMARY OF THE INVENTION

The invention provides an atrial cardioverter for cardioverting atria of a heart while sustaining atrial pacing of the heart. The cardioverter includes a pacer for pacing the heart in one of a plurality of modes including an atrial pacing, atrial inhibited mode, and an atrial pacing, ventricular inhibited mode and an atrial tachyarrhythmia detector for detecting an atrial tachyarrhythmia of the heart. The cardioverter further includes means for changing the mode of the pacer from the atrial pacing, atrial inhibited mode to the atrial pacing, ventricular inhibited mode responsive to the atrial tachyarrhythmia detector detecting an atrial tachyarrhythmia of the heart and a cardioverting stage for applying cardioverting energy to the atria responsive to the atrial tachyarrhythmia detector detecting an atrial tachyarrhythmia and after the pacer mode change.

The invention further provides an atrial cardioverter for cardioverting atria of a heart while sustaining atrial pacing of the heart. The cardioverter includes a pacer for pacing the heart in one of a plurality of modes including an atrial pacing, atrial inhibited mode and an atrial pacing, atrial and ventricular inhibited mode and an atrial tachyarrhythmia detector for detecting an atrial tachyarrhythmia of the heart. The cardioverter further includes means for changing the mode of the pacer from the atrial pacing, atrial inhibited mode to the atrial pacing, atrial and ventricular inhibited mode responsive to the atrial tachyarrhythmia detector detecting an atrial tachyarrhythmia of the heart and a cardioverting stage for applying cardioverting energy to the atria responsive to the atrial tachyarrhythmia detector detecting an atrial tachyarrhythmia and after the pacer mode change.

The invention still further provides a method of cardioverting atria of a heart while sustaining atrial pacing of the heart. The method includes the steps of pacing the heart in an atrial pacing, atrial inhibited mode detecting an atrial tachyarrhythmia of the heart, changing the pacing mode from the atrial pacing, atrial inhibited mode to an atrial pacing, ventricular inhibited mode responsive to detecting an atrial tachyarrhythmia of the heart, and applying cardioverting energy to the atria responsive to detecting an atrial tachyarrhythmia and after the pacer mode change.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the several figures of which like reference numerals identify identical elements, and wherein;

DETAILED DESCRIPTION OF THE PREFERRED EMBODIMENT

Figure 1:
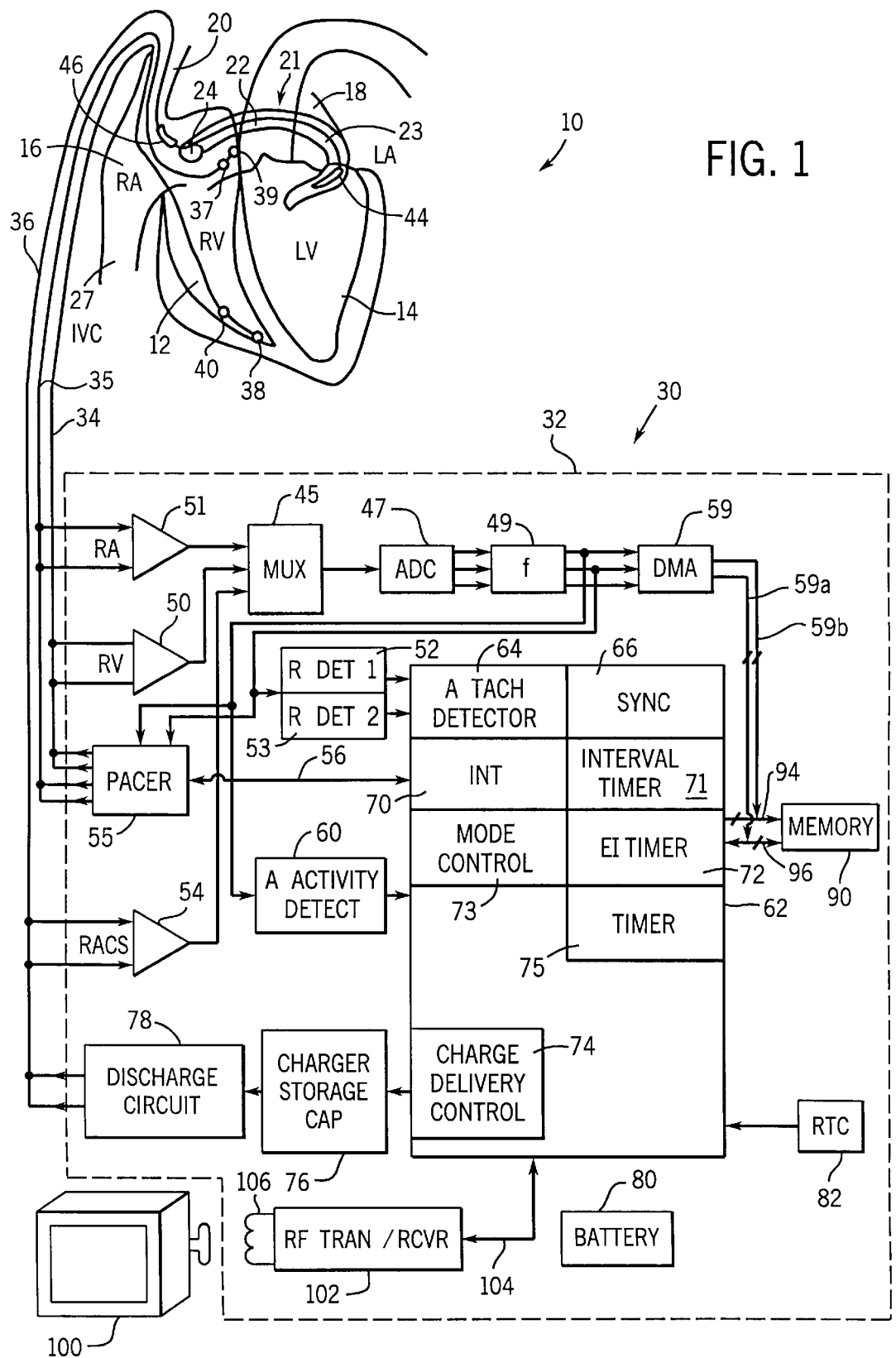
FIG. 1 is a schematic block diagram of a fully implantable atrial cardioverter/defibrillator embodying the present invention.

Prior to referring to FIG. 1, a general description of a typical or normal cardiac cycle may be helpful in understanding the operation and various aspects of the present invention. The beginning of a cardiac cycle in normal sinus rhythm is initiated by a P wave which is normally a small positive wave. The P wave results from depolarization of the atria of the heart. Following the P wave there is a cardiac cycle portion which is substantially constant having a time duration on the order of, for example, 120 milliseconds.

The QRS complex of the cardiac cycle then normally occurs after the substantially constant portion. The dominating feature of the QRS complex is the R wave which is a rapid positive or negative deflection. The R wave generally has an amplitude greater than any other wave of the cardiac cycle and is characterized by a rapid deviation from and return toward baseline. The R wave results from the depolarization of the ventricles. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds.

Referring now to FIG. 1, it illustrates a fully implantable atrial cardioverter/defibrillator 30 embodying the present invention shown in association with a schematically illustrated human heart 10. The portions of the heart 10 illustrated in the sole figure are the right ventricle 12, the left ventricle 14, the right atrium 16, the left atrium 18, the superior vena cava 20, the coronary sinus channel 21 which, as used herein, denotes the coronary sinus 22 and the great cardiac vein 23, the coronary sinus ostium or opening 24, and the inferior vena cava 27.

The atrial defibrillator 30 generally includes an enclosure 32 for hermetically sealing the internal circuit elements of the atrial defibrillator to be described hereinafter, a ventricular endocardial or first lead 34, a right atrial endocardial or second lead 35 and an intravascular or third lead 36. The enclosure 32 and leads 34, 35, and 36 are arranged to be implanted beneath the skin of a patient so as to render the atrial defibrillator 30 fully implantable.

The intravascular lead 36 generally includes a first or tip electrode 44 and a second proximal electrode 46. As illustrated, the lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18. The first electrode 44 and the second electrode 46 are further used to deliver defibrillating electrical energy to the atria. The electrodes 44 and 46 are preferably elongated cardioverting electrodes.

The first lead 34 preferably comprises a ventricular endocardial lead having bi-polar pair electrodes 38 and 40 arranged for establishing electrical contact with the right ventricle 12 of the heart 10. The electrodes 38 and 40 permit bi-polar sensing of ventricular activations in the right ventricle and pacing in the right ventricle. As illustrated, the lead 34 is fed through the superior vena cava 20, into the right atrium 16, and then into the right ventricle 12.

The second lead 35 preferably comprises a right atrial endocardial lead having bi-polar pair electrodes 37 and 39. Electrode 39 preferably is a helical screw-in coil for both providing fixation of the lead 35, as known in the art, and establishing electrical contact with the right atrium 16 of the heart 10. The electrodes 37 and 39 permit localized bi-polar sensing of heart activity in the right atrium and pacing, including fixed or rate responsive pacing, in the right atrium. As illustrated, the lead 35 is fed through the superior vena cava 20 and into the right atrium 16.

Within the enclosure 32, the atrial defibrillator 30 includes a first sense amplifier 50, a second sense amplifier 51, a third sense amplifier 54 and a multiplexer 45. The first sense amplifier 50 forms an RV channel which provides an electrogram of the sensed right ventricular heart activity at an input of the multiplexer 45. The second sense amplifier 51 forms an RA channel to provide an electrogram of the sensed right atrial heart activity at its output which is coupled to another input of multiplexer 45. The third sense amplifier 54 forms an RACS channel to provide an electrogram of the sensed right atrium to left atrium heart activity at its output which is coupled to another input of the multiplexer 45. The sense amplifiers may include a differentiating filter so that the electrograms which they provide are differentiated electrogram signals.

The multiplexer 45 provides analog samples of the RA, RV, and RACS electrograms, one at a time, to an analog to digital converter (ADC) 47. The ADC 47 digitizes the electrograms and provides them at a respective output to a digital bandpass filter 49. The filter 49 is of the type well known in the art which provides both a high and low bandpass function. The digitized and filtered RA, RV, and RACS electrograms are each provided at a respective dedicated filter output. All three electrograms are provided to a direct memory access (DMA) 59. The RA electrogram is also provided to a pacer 55 and an atrial activity detector 60. The RV electrogram is also provided to the pacer 55 and first and second R wave detectors 52 and 53.

The atrial activity detector 60 is continuously provided with the digitized RA electrogram. When the detector 60 determines that the atrial activity rate exceeds a predetermined rate, it causes an atrial therapy intervention to be initiated. The atrial intervention therapy shall be described subsequently.

The R wave detectors 52 and 53 detect R waves from the digitized RV electrogram. The R wave detector 52 is more sensitive and less specific for detecting R waves than the R wave detector 53. To that end, the R wave detector 52 has a lower threshold than R wave detector 53. The R wave detector 52 is used to reset a cardiac interval timer which times time spans between R waves while the more specific and less sensitive R wave detector 53 is used to synchronize the delivery of cardioverting energy to the atria with an R wave.

The enclosure 32 of the atrial defibrillator 30 further includes a microprocessor 62. The microprocessor 62 is preferably implemented in accordance with this embodiment of the present invention to result in a plurality of functional stages. The stages include an atrial tachyarrhythmia detector, preferably in the form of an atrial fibrillation detector 64, a synchronization stage 66, an interrupt stage 70, a cardiac interval timer 71, an escape interval timer 72, a mode control 73, and a charge delivery and energy control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or receiver programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from the external controller 100 and for transmitting data to the external controller 100. One preferred communication system is disclosed in copending U.S. Pat. No. 5,342,408 which issued on Aug. 30, 1994 for "Telemetry System for an Implantable Cardiac Device," which patent is assigned to the assignee of the present invention and incorporated herein by reference.

A data acquisition is performed to determine if there is an atrial tachyarrhythmia of the heart and, if there is, to determine if electrogram amplitudes are of sufficient amplitude and quality to support safe delivery of the cardioverting energy. The thresholds of R wave detectors 52 and 53 are also set based upon this last mentioned data acquisition. During a data acquisition, the analog to digital converter 47 converts the RA, RV, and RACS electrogram signals into digital data. The digital data is received by the DMA 59 and conveys the digital data to memory 90 over a data bus 59a for storage in memory at predetermined locations selected by the DMA 59 over an address bus 59b. The electrogram signals thus stored in digital form representing activity of the heart are thereafter utilized by the microprocessor to perform various functions. For example, for atrial fibrillation detection, the atrial fibrillation detector 64 preferably utilizes the stored data from the RACS channel for detecting the presence of atrial fibrillation of the heart.

The atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. The defibrillator 30 further includes a depletable power source 80, such as a lithium battery, for providing power to the electrical components of the atrial defibrillator 30, and a real time clock 82.

The atrial defibrillator 30 lastly includes a pacer 55 which is coupled to electrodes 38 and 40 of lead 34 and to electrodes 37 and 39 of lead 35. The pacer 55 preferably utilizes the digitized RV electrograms for sensing ventricular activity and includes pacing circuitry for applying pacing pulses to the ventricles with electrodes 38 and 40. Similarly, the pacer 55 preferably utilizes the digitized RA electrogram for sensing atrial activity and includes pacing circuitry for applying pacing pulses to the atria with electrodes 37 and 39. Further, the pacer 55 may provide single chamber pacing in either the right ventricle 12 or right atrium 16, asynchronously or on demand, or dual chamber pacing. Such pacers and modalities are well known in the art. The pacer is coupled to the microprocessor over a line 56 to permit the microprocessor to configure the pacer 55 for any one of its pacing modalities including, in accordance with the present invention, an atrial pacing/atrial inhibited (AAI or AAIR) modality, an atrial pacing/ventricular inhibited (AVI) modality, or an atrial pacing/ventricular and atrial inhibited (ADI) pacing modality. The line 56 also provides a means by which the pacer 55 can provide the interrupt stage 70 with an input signal whenever the pacer 55 applies a pacing pulse to the heart. Also, the line 56 may be further used for the microprocessor 62 to command the pacer 55 to apply a pacing pulse when the microprocessor takes over escape interval timing from the pacer 55.

The following discussion assumes that the pacer has been placed into a continuous atrial pacing mode such as the AAI or AAIR mode. At predetermined times as described in U.S. Pat. No. 5,464,432 or based upon continuously monitored heart activity by the atrial activity detector, an atrial fibrillation detection is initiated. A data acquisition is first performed for a data acquisition period of, for example, eight seconds. During the eight second data acquisition period, the digitized RACS, RA, and RV electrograms are caused to be stored in the memory 90 by the DMA 59 as previously described.

After the eight second data acquisition period is completed, the atrial fibrillation detector 64 is enabled and analyzes the stored electrogram data from the RACS channel. The atrial fibrillation detector 64 may determine if the atria 16 and 18 are in fibrillation in a manner as described, for example, in U.S. Pat. No. 5,486,199 which issued on Jan. 13, 1996 for "System and Method For Reducing False Positives In Atrial Fibrillation Detection," which patent is assigned to the assignee of the present invention and incorporated herein by reference. If the atria are in fibrillation and thus in need of cardioversion, the charge delivery control 74 causes the charger and storage capacitor circuit 76 to charge the storage capacitor within the circuit 76 to a selected peak voltage. After the capacitor is charged, another data acquisition is performed and the atrial fibrillation detector 64 confirms the presence of atrial fibrillation.

After the continued existence of atrial fibrillation is confirmed, another data acquisition, preferably lasting eight seconds, for example, is performed. The stored electrograms from this acquisition are used to set the thresholds of R wave detectors 52 and 53 and to confirm that the electrograms are of sufficient quality and amplitude to support cardioverting energy delivery.

If the foregoing is successfully completed, in accordance with a preferred embodiment of the present invention, the microprocessor 62 through mode control 73, changes the mode of pacer 55 from the atrial pacing, atrial inhibited (AAI or AAIR) mode to an atrial pacing, ventricular inhibited (AVI) mode. The microprocessor also assumes control of escape interval timing through the escape interval timer 72. The escape interval timer is reset by the more specific and less sensitive R wave detector 53. Hence, in this pacing mode, if there is no R wave detected for a low rate interval of, for example, 800 to 1200 milliseconds, then the microprocessor commands the pacer 55 to deliver a pacing pulse to the atria. Hence, the AVI mode is functionally equivalent to the VVI mode except that pacing ocurs in an atrium rather than in a ventricle. In addition, a refractory period is preferably provided to take the A-V conduction time into account. In this manner, needed atrial pacing is provided.

The defibrillator 30 then proceeds into a real time synchronization routine while continuing the AVI pacing. The synchronization stage analyzes the R waves detected by the more sensitive R wave detector 52 to locate a safe time to deliver therapy. The cardiac interval timer 71 times time spans between immediately successive R waves detected with R wave detector 52. When such a time span exceeds a predetermined minimum duration, such as 500 milliseconds, for example, the synchronization stage 66 causes the charge delivery and storage control 74 to discharge the storage capacitor of circuit 76 to apply the cardioverting energy to electrodes 44 and 46, and thus the atria. To assure that the time span between immediately successive R waves is free of atrial pacing pulses, the commands by the microprocessor to the pacer 55 to pace the atria over line 56 to pace the atria are also used to reset the cardiac interval timer 71.

Figure 2:
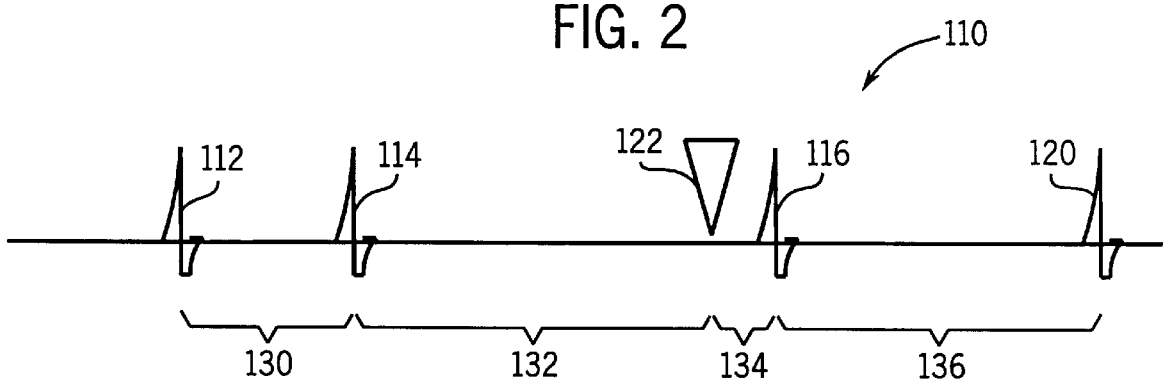
FIG. 2 is an electrogram illustrating the operation of the present invention in accordance with a preferred embodiment thereof.

FIG. 2 illustrates the foregoing operation. The electrogram 110 includes detected R waves 112, 114, 116, and 120 and an atrial pacing pulse 122. The timers 71 and 72 time the time spans 130, 132, 134, and 136 between each R wave and atrial pacing pulse. As illustrated, time span 130 is too short to cause either a pacing pulse or cardioverting energy delivery. Hence, both timers 71 and 72 are reset by R wave 114. Time span 132 completes a ventricular escape interval timed by time 72 causing the atrial pacing pulse 122 to be delivered. Time span 134 is too short for either pacing or cardioverting energy delivery. However, time span 136 between R waves 116 and 120 is longer than the minimum interval but shorter than the escape interval. Hence, cardioverting energy may be delivered synchronized to R wave 120 if the more specific R wave detector 53 detects it. Hence, as can be seen, the present invention permits atrial tachyarrhythmia cardioversion while maintaining necessary atrial pacing. In accordance with a further aspect of the present invention, the atrial pacing/ventricular inhibited mode of pacing may be the atrial pacing/ventricular and atrial inhibited (ADI) mode. This mode, is functionally equivalent to the DDI mode with ventricular pacing suppressed or disabled and a post ventricular atrial refractory period (PVARP) provided only long enough to provide a post atrial pacing atrial refractory period. A further timer 75 may be employed in this mode for timing the additionally escape interval.

While particular embodiments of the present invention have been shown and described, modifications may be made. It is therefore intended in the appended claims to cover all such changes and modifications which fall within the true spirit and scope of the invention.

What is claimed is:

1. An atrial cardioverter for cardioverting atria of a heart while sustaining atrial pacing of the heart, the cardioverter comprising:

a pacer for pacing the heart in one of a plurality of modes including an atrial pacing, atrial inhibited mode, and an atrial pacing, ventricular inhibited mode;

an atrial tachyarrhythmia detector for detecting an atrial tachyarrhythmia of the heart;

means for changing the mode of the pacer from the atrial pacing, atrial inhibited mode to the atrial pacing, ventricular inhibited mode responsive to the atrial tachyarrhythmia detector detecting an atrial tachyarrhythmia of the heart; and a cardioverting stage for applying cardioverting energy to the atria responsive to the atrial tachyarrhythmia detector detecting an atrial tachyarrhythmia and after the pacer mode change.

2. A cardioverter as defined in claim 1 including an R wave detector for detecting R waves of the heart and an escape interval timer responsive to the R wave detector for timing escape intervals when the pacer is in the atrial pacing, ventricular inhibited mode.

3. A cardioverter as defined in claim 1 further including a cardiac interval timer for timing time spans of cardiac cycles and wherein the cardioverting stage is responsive to the cardiac interval timer for applying cardioverting energy to the atria when a time span is greater than a minimum interval.

4. A cardioverter as defined in claim 3 wherein the cardioverting stage is further responsive to R wave detection for applying the cardioverting energy synchronized to an R wave.

5. A cardioverter as defined in claim 3 further comprising an escape interval timer for timing escape intervals when the pacer is in the atrial pacing, ventricular inhibited mode, a first R wave detector for resetting the escape interval timer and a second R wave detector for resetting the cardiac interval timer, the first R wave detector being more specific than the second R wave detector for detecting R waves.

6. A cardioverter as defined in claim 5 further including means for causing the cardiac interval timer to be further reset responsive to atrial pacing by the pacer.

7. A cardioverter as defined in claim 1 wherein the pacer is further arranged for pacing the heart in an atrial pacing, ventricular and atrial inhibited mode.

8. An atrial cardioverter for cardioverting atria of a heart while sustaining atrial pacing of the heart, the cardioverter comprising:

a pacer for pacing the heart in one of a plurality of modes including an atrial pacing, atrial inhibited mode and an atrial pacing, atrial and ventricular inhibited mode;

an atrial tachyarrhythmia detector for detecting an atrial tachyarrhythmia of the heart;

means for changing the mode of the pacer from the atrial pacing, atrial inhibited mode to the atrial pacing atrial and ventricular inhibited mode responsive to the atrial tachyarrhythmia detector detecting an atrial tachyarrhythmia of the heart; and a cardioverting stage for applying cardioverting energy to the atria responsive to the atrial tachyarrhythmia detector detecting an atrial tachyarrhythmia and after the pacer mode change.

9. A cardioverter as defined in claim 8 further including an R wave detector for detecting R waves of the heart and a cardiac interval timer responsive to the R wave detector for timing time spans of cardiac intervals, and wherein the cardioverting stage is responsive to the cardiac interval timer for applying cardioverting energy to the atria when a time span is greater than a minimum interval.

10. A method of cardioverting atria of a heart while sustaining atrial pacing of the heart, the method including the steps of:

pacing the heart in an atrial pacing, atrial inhibited mode;

detecting an atrial tachyarrhythmia of the heart;

changing the pacing mode from the atrial pacing, atrial inhibited mode to an atrial pacing, ventricular inhibited mode responsive to detecting an atrial tachyarrhythmia of the heart; and applying cardioverting energy to the atria responsive to detecting an atrial tachyarrhythmia and after the pacer mode change.

11. A method as defined in claim 10 wherein the atrial pacing, ventricular inhibited mode is an atrial pacing, atrial and ventricular inhibited mode.

* * * * *